US012115046B2

United States Patent
Schlörmann et al.

(10) Patent No.: US 12,115,046 B2
(45) Date of Patent: Oct. 15, 2024

(54) METHOD AND DEVICE FOR FORMING GROUPS OF COMPRESSED HYGIENE PRODUCTS

(71) Applicant: Focke & Co. (GmbH & Co. KG), Verden (DE)

(72) Inventors: Marco Schlörmann, Moormerland (DE); Matthias Vocks, Strücklingen (DE)

(73) Assignee: Focke & Co. (GmbH & Co. KG), Verden (DE)

( * ) Notice: Subject to any disclaimer, the term of this patent is extended or adjusted under 35 U.S.C. 154(b) by 0 days.

(21) Appl. No.: 17/908,963

(22) PCT Filed: Mar. 9, 2021

(86) PCT No.: PCT/EP2021/055950
§ 371 (c)(1),
(2) Date: Jan. 17, 2023

(87) PCT Pub. No.: WO2021/185633
PCT Pub. Date: Sep. 23, 2021

(65) Prior Publication Data
US 2024/0277531 A1    Aug. 22, 2024

(30) Foreign Application Priority Data
Mar. 17, 2020   (DE) .................... 10 2020 001 752.5

(51) Int. Cl.
*A61F 13/15*    (2006.01)
*B65B 35/24*    (2006.01)
(Continued)

(52) U.S. Cl.
CPC .. *A61F 13/15764* (2013.01); *A61F 13/15707* (2013.01); *B65B 35/243* (2013.01);
(Continued)

(58) Field of Classification Search
None
See application file for complete search history.

(56) References Cited

U.S. PATENT DOCUMENTS

| 3,370,549 A | 2/1968 | Livingston |
| 5,195,300 A * | 3/1993 | Kovacs ................ B65B 63/026 |
| | | 100/207 |

(Continued)

FOREIGN PATENT DOCUMENTS

| DE | 102011107290 A1 | 1/2013 |
| DE | 112011102471 T5 | 4/2013 |

(Continued)

OTHER PUBLICATIONS

Deutsches Patent—Und Markenamt (German Patent and Trademark Office), Recherchebericht (search in a related application), Dec. 3, 2020.

(Continued)

*Primary Examiner* — Kavel Singh
(74) *Attorney, Agent, or Firm* — Laurence P. Colton; Smith Tempel Blaha LLC

(57) ABSTRACT

A method and device for forming groups of compressed hygiene products, wherein uncompressed hygiene products are supplied by a first conveyor and are transferred to a compressing apparatus having a compartment for a group of uncompressed hygiene products, and a plurality of uncompressed hygiene products are transferred from the first conveyor into the compartment while the compartment is moved, together with the first conveyor, in a transport direction. The group of uncompressed hygiene products is compressed in the compartment during the transporting in the transport direction such that, after compression, a group of compressed hygiene products is situated in the compartment, and the group of compressed hygiene products is discharged to a compartment of a second conveyor during (Continued)

the further transporting of the compartment of the compressing apparatus, wherein the compartment of the compressing apparatus is moved in the transport direction with the compartment of the second conveyor.

22 Claims, 8 Drawing Sheets

(51) Int. Cl.
*B65B 63/02* (2006.01)
*B65G 47/26* (2006.01)
*B65G 47/68* (2006.01)
*B65G 57/03* (2006.01)

(52) U.S. Cl.
CPC .......... *B65B 63/022* (2013.01); *B65G 47/268* (2013.01); *B65G 47/68* (2013.01); *B65G 57/03* (2013.01); *B65G 2201/02* (2013.01)

(56) References Cited

U.S. PATENT DOCUMENTS

| | | | | |
|---|---|---|---|---|
| 6,708,465 | B1* | 3/2004 | Gustafsson | B65B 51/20 |
| | | | | 53/529 |
| 6,708,468 | B2* | 3/2004 | Kondou | G07F 11/1657 |
| | | | | 53/247 |
| 8,015,751 | B2* | 9/2011 | Weder | B65B 25/02 |
| | | | | 47/72 |
| 10,246,203 | B2* | 4/2019 | Rasi | B65B 35/44 |
| 10,450,095 | B2* | 10/2019 | Brandhorst | B65B 35/44 |
| 2015/0203231 | A1* | 7/2015 | Brandhorst | B65B 57/005 |
| | | | | 100/90 |

FOREIGN PATENT DOCUMENTS

| | | |
|---|---|---|
| EP | 2729374 B1 | 5/2014 |
| EP | 2885213 B1 | 6/2015 |
| EP | 3473564 A1 | 4/2019 |
| WO | 2013004325 A1 | 1/2013 |
| WO | 2014029481 A1 | 2/2014 |

OTHER PUBLICATIONS

WIPO, International Search Report (in a related application), Jun. 7, 2021.

* cited by examiner

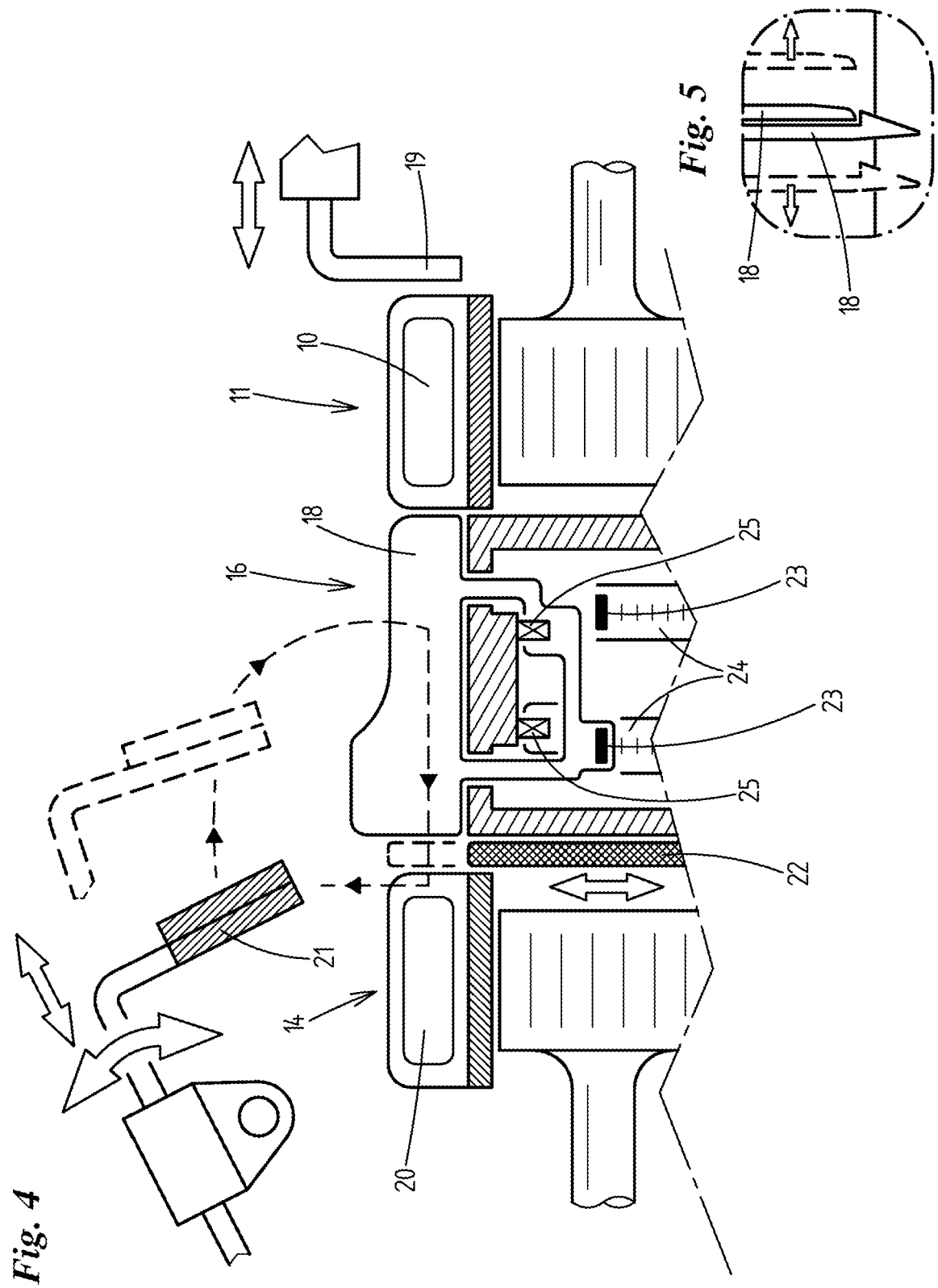

METHOD AND DEVICE FOR FORMING GROUPS OF COMPRESSED HYGIENE PRODUCTS

CROSS REFERENCE TO RELATED APPLICATIONS

This application is the US national phase of and claims the benefit of and priority on International Application No. PCT/EP2021/055950 having an international filing date of 9 Mar. 2021, which claims priority on and the benefit of German Patent Application No. 10 2020 001 752.5 having a filing date of 17 Mar. 2020.

BACKGROUND OF THE INVENTION

Technical Field

The invention relates to a method for forming groups of compressed hygiene products, wherein uncompressed hygiene products are supplied by a continuously driven first conveyor and are transferred from the first conveyor to a compressing apparatus during the continuous transporting, wherein the compressing apparatus has at least one compartment for a group of uncompressed hygiene products, and wherein in each case a plurality of uncompressed hygiene products are transferred from the first conveyor into the compartment of the compressing apparatus whilst the compartment is moved continuously, together with the first conveyor, in the transport direction of the latter.

The invention moreover relates to a corresponding device for forming groups of compressed hygiene products, with a continuously driven first conveyor for supplying uncompressed hygiene products, and with a compressing apparatus for receiving the uncompressed hygiene products from the first conveyor during the continuous transporting, wherein the compressing apparatus has at least one compartment for a group of uncompressed hygiene products, and wherein the device is configured to transfer in each case a plurality of uncompressed hygiene products from the first conveyor into the compartment of the compressing apparatus whilst the compartment is moved continuously, together with the first conveyor, in the transport direction of the latter.

Prior Art

Methods and devices for handling and compressing hygiene articles are already known in different variants from the prior art. Thus, EP 2 729 374 B1 discloses a solution in which hygiene products are brought together to form compressed groups before being conveyed away. The groups of hygiene products are here compressed by means of rigid guides before being transferred to a removal conveyor.

EP 2 885 213 B1 discloses a solution for handling hygiene articles, in which two compressing members grip a group of hygiene articles and compress them to a delivery size during the movement. This group is then transferred to a second, stationary compressing unit before it is finally conveyed away.

BRIEF SUMMARY OF THE INVENTION

Against this background, the object of the invention is to further develop methods and devices of the type mentioned at the beginning, in particular with regard to a higher capacity.

In order to achieve this object, a method according to the invention is a method for forming groups of compressed hygiene products, wherein uncompressed hygiene products are supplied by a continuously driven first conveyor and are transferred from the first conveyor to a compressing apparatus during the continuous transporting, wherein the compressing apparatus has at least one compartment for a group of uncompressed hygiene products, and wherein in each case a plurality of uncompressed hygiene products are transferred from the first conveyor into the compartment of the compressing apparatus whilst the compartment is moved continuously, together with the first conveyor, in the transport direction of the latter, characterized in that the group of uncompressed hygiene products is compressed in the compartment during the continuous transporting in the transport direction such that, after compression, a group of compressed hygiene products is situated in the compartment of the compressing apparatus, and wherein the group of compressed hygiene products is discharged to a compartment of a second conveyor during the further continuous transporting of the compartment of the compressing apparatus in the transport direction, wherein the compartment of the compressing apparatus is moved continuously in the transport direction with the compartment of the second conveyor. It is accordingly provided that the group of uncompressed hygiene products is compressed in the compartment during the continuous transporting in the transport direction such that, after compression, a group of compressed hygiene products is situated in the compartment of the compressing apparatus, and wherein the group of compressed hygiene products is discharged to a compartment of a second conveyor during the further continuous transporting of the compartment of the compressing apparatus in the transport direction, wherein the compartment of the compressing apparatus is moved continuously in the transport direction with the compartment of the second conveyor.

The applicant has identified that the intermittent operation, known from the prior art, of the devices limits the speed of the latter because the non-continuous transporting and/or the non-continuous intermediate processing of the products always requires multiple cycles. The same also applies for the stepwise compressing of the products in successive stations. Processing processes which are performed in cycles or stepwise require appropriate pauses (with the elements of the machine at a standstill) between the cycles, which limits the production capacity of such machines. A further disadvantage of devices working in cycles with a high production capacity is the masses which need to be accelerated which cause high stresses during operation in cycles (constantly repeated acceleration/deceleration procedures). These problems known from the prior art are obviated by the continuous operation of the device.

It can preferably be provided that the at least one compartment of the compressing apparatus is limited laterally by opposite walls of the compressing apparatus which are moved toward each other in order to compress the group of uncompressed hygiene products whilst the compartment is moved continuously in the transport direction.

In a preferred embodiment of the invention, it can be provided that the compartment of the compressing apparatus is moved respectively synchronously with the first conveyor or the second conveyor continuously in the transport direction in order to receive the uncompressed hygiene products and/or discharge the compressed hygiene products.

It can preferably be provided that, during the transfer of the uncompressed hygiene products to the compressing apparatus, in each case a plurality of adjacent compartments of the compressing apparatus are filled simultaneously with a plurality of hygiene products whilst the compartments are moved continuously with the first conveyor in the transport direction. The compressing of the hygiene products situated in at least some adjacent compartments preferably takes place simultaneously.

This solution has in particular the advantage that in this way the production capacity of the device is further increased.

As an alternative or in addition, it can be provided that, when the compressed hygiene products are discharged from the compressing apparatus, in each case a plurality of groups of compressed hygiene products are transferred simultaneously to a plurality of adjacent compartments of the second conveyor whilst the compartments of the compressing apparatus and the compartments of the second conveyor are moved continuously in the transport direction.

A further special feature can consist in the compressing apparatus equalizing differences in speed between the first conveyor and the second conveyor, wherein the difference in speed can also be equal to zero such that the first conveyor and the second conveyor are driven in the transport direction at the same speed.

The compressing apparatus arranged between the two conveyors can in other words serve to equalize different speeds of the two conveyors and match alternately one or the other speed. If the two conveyors are being operated at the same speed, of course no matching of the speeds is necessary.

It can accordingly be provided that the first conveyor and the second conveyor are driven in the transport direction at a matching speed and that the compartments of the compressing unit are moved at the same speed in the transport direction when receiving the uncompressed hygiene products and when discharging the compressed hygiene products.

It can alternatively be provided that the first conveyor and the second conveyor are driven in the transport direction at different speeds and that the at least one compartment of the compressing unit is, when receiving the uncompressed hygiene products and discharging the compressed hygiene products, moved in the transport direction at a speed which corresponds respectively to the speed of the first conveyor and of the second conveyor.

A further special feature can consist in the compressing of the hygiene products taking place exclusively in the compressing unit, and in particular there being no upstream or downstream pre-compressing or post-compressing.

In a preferred embodiment of the invention, it can be provided that the movement of the walls of the at least one compartment of the compressing apparatus is superimposed with the transporting of the at least one compartment in the transport direction during the compression of the group of hygiene products in the at least one compartment.

It can structurally moreover be provided that the uncompressed hygiene products are transferred from the first conveyor to the compressing unit by means of a first pusher, wherein the uncompressed hygiene products are pushed away, transversely to the transport direction of the first conveyor and of the compressing unit, by means of the first pusher.

It can structurally moreover be provided that the at least one group of compressed hygiene products is pulled out from the compartments of the compressing unit and across onto the second conveyor by means of an extraction member, wherein the group of compressed hygiene products is pulled across by means of the extraction member transversely to the transport direction of the compressing unit and of the second conveyor.

The conveyors can be arranged such that the product flow on the first conveyor, in the compressing apparatus, and on the second conveyor runs in mutually parallel paths at least in the respective transfer region of the uncompressed hygiene products or the at least one group of compressed hygiene products.

A further special feature can consist in a grouping apparatus, which continuously runs at least temporarily in the transport direction, being provided between the compressing apparatus and the second conveyor, wherein the grouping apparatus has at least one compartment into which groups of compressed hygiene products coming from the compressing apparatus are pushed, wherein the grouping apparatus or the at least one compartment thereof and the compressing apparatus of the at least one compartment thereof are stationary during the transfer.

It is preferably provided that the plurality of groups of compressed hygiene products are transferred one after the other to the compartment of the grouping apparatus by a pusher in such a way that the groups are arranged one behind the other in the pushing direction.

It can alternatively be provided that the plurality of groups are transferred together to the compartment of the grouping apparatus.

It can furthermore be provided that the plurality of groups of compressed hygiene products are together pulled out from the compartment of the grouping apparatus and across onto the second conveyor by the extraction member whilst the grouping apparatus or the at least one compartment thereof is moved continuously in the transport direction together with the second conveyor or the at least one compartment thereof.

It is alternatively in turn conceivable that the extraction member pulls across the groups one after the other from the compartment of the grouping apparatus, and/or that this takes place whilst the grouping apparatus is at a standstill for a short time.

It is preferably provided that in each case a plurality of groups of compressed hygiene products are transferred simultaneously from adjacent compartments of the compressing apparatus to the grouping apparatus and/or from the grouping apparatus to the second conveyor.

A device for achieving the object mentioned at the beginning is a device for forming groups of compressed hygiene products, with a continuously driven first conveyor for supplying uncompressed hygiene products, and with a compressing apparatus for receiving the uncompressed hygiene products from the first conveyor during the continuous transporting, wherein the compressing apparatus has at least one compartment for a group of uncompressed hygiene products, and wherein the device is configured to transfer in each case a plurality of uncompressed hygiene products from the first conveyor into the compartment of the compressing apparatus whilst the compartment is moved continuously, together with the first conveyor, in the transport direction of the latter, characterized in that the device is configured to compress the group of uncompressed hygiene products in the compartment of the compressing apparatus during the continuous transporting in the transport direction such that, after compression, a group of compressed hygiene products is situated in the compartment of the compressing apparatus, and wherein the device is moreover configured to discharge the group of compressed hygiene products to a compartment of a second conveyor during the further continuous transporting of the compartment of the compressing apparatus in the transport direction, wherein the compartment of the compressing apparatus is moved continuously in the transport direction with the compartment of the second conveyor. It is accordingly provided that the device is configured to compress the group of uncompressed hygiene products in the compartment during the continuous transporting in the transport direction such that, after compression, a group of compressed hygiene products is situated in the compartment of the compressing apparatus, and wherein the device is moreover configured to discharge the group of compressed hygiene products to a compartment of a second conveyor during the further continuous transporting of the compartment of the compressing apparatus in the transport direction, wherein the compartment of the compressing apparatus is moved with the compartment of the second conveyor continuously in the transport direction.

It can furthermore be provided that the at least one compartment of the compressing apparatus is limited laterally by opposite walls of the compressing apparatus, and that the walls of the at least one compartment can be moved toward each other by one or more drives in order to compress the group of uncompressed hygiene products.

It can in particular be provided that the two opposite walls of the at least one compartment are each coupled to a transmission means, in particular a belt, which can be driven by in each case one independent drive associated with the respective transmission means in order to move the walls of the at least one compartment.

It can be preferred that, in the case of a compressing apparatus with a plurality of compartments, first walls of each compartment are coupled to a first transmission means and second walls of each compartment are coupled to the second transmission means such that two groups of walls are formed which in each case can be moved together by drives associated with the transmission means.

It is furthermore conceivable that, in the case of a compressing apparatus with a plurality of compartments, each wall of each compartment is coupled to a separate independent transmission means which can be driven by an independent drive in order to individually move each wall of all the compartments.

It can preferably be provided that adjacent walls of adjacent compartments of the compressing apparatus are formed so that they engage inside each other in a space-saving manner.

BRIEF DESCRIPTION OF THE DRAWINGS

Preferred exemplary embodiments of the invention are described below with the aid of the drawings, in which:

FIG. 4 shows a vertical section through the device along the line of section IV-IV in FIG. 3;

FIG. 5 shows a detail of the device in an enlarged illustration; and

DETAILED DESCRIPTION OF PREFERRED EMBODIMENTS

Figure 1:
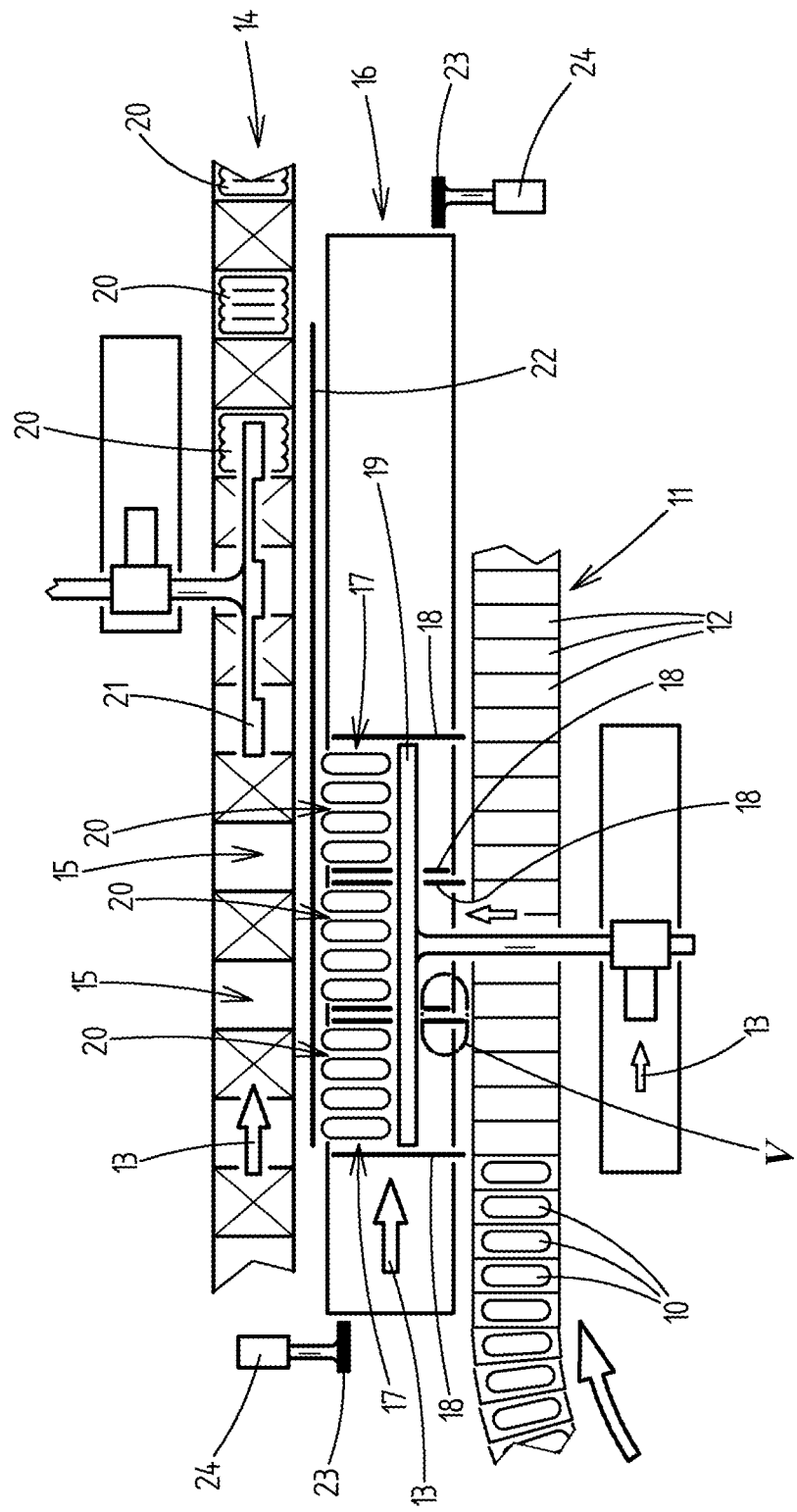
FIGS. 1 to 3 show a device for forming compressed groups of hygiene products in a plan view during successive phases of the movement sequence.

The invention is described below with the aid of two devices for forming compressed groups of hygiene products. The hygiene products 10 can, for example, be sanitary towels. For example, diapers, make-up removal pads, or pulp products in general are, however, also conceivable.

The hygiene products 10 are supplied to a first conveyor 11 which can be designed, for example, as a compartmentalized conveyor belt.

The first conveyor 11 has a plurality of compartments 12 in which the hygiene products 10 are arranged. In each case one product 10 is preferably situated in each compartment 12. It is, however, also conceivable that a plurality of hygiene products 10 are situated in a compartment 12, for example in the form of a bundle or as a loose group. The hygiene products 10 are preferably arranged vertically or horizontally in the compartments 12.

The first conveyor 11 is driven continuously in a transport direction 13. The hygiene products 10 are arranged in the compartments 12 with their longitudinal extent transverse to the transport direction 13.

A second conveyor 14 serves to transport the hygiene products 10 away.

The second conveyor 14 also has compartments 15 and is driven continuously in the transport direction 13. The second conveyor 14 can be designed, for example, as a pocket chain conveyor.

A compressing apparatus 16 runs between the first conveyor 11 and the second conveyor 14. The compressing apparatus 16 also has compartments 17 which serve to receive the hygiene products 10 and can be moved continuously in the transport direction.

The compartments 17 of the compressing apparatus 16 are each limited by opposite walls 18. The walls 18 run transversely, in particular perpendicularly, to the transport direction 13 or the longitudinal extent of the compressing apparatus 16.

In order to transfer the hygiene products 10 from the first conveyor 11 to the compressing apparatus 16 and from the compressing apparatus 16 to the second conveyor 14, the first conveyor 11, the second conveyor 14, and the compressing apparatus 16 run essentially parallel to one another at least in the transfer region of the hygiene products 10.

A pusher 19, by means of which the hygiene products 10 are pushed from the compartments 12 of the first conveyor 11 into the compartments 17 of the compressing apparatus 16, serves to transfer the hygiene products 10 from the first conveyor 11 to the compressing apparatus 16.

The pusher 19 preferably works together with a stop 22 which limits the pushing movement of the hygiene products 10 and is arranged between the compressing apparatus 16 and the second conveyor 14 in such a way that the hygiene products 10 cannot be pushed beyond the compartments 17 of the compressing apparatus 16 by the pusher 19.

A special feature consists in this taking place during the continuous transporting. The compartments 12 and 17 are accordingly moved together with the pusher 19 in the transport direction 13 during the transfer.

It can be seen from the drawings, in particular from FIG. 1, that the alignment of the hygiene products 10 does not change here. However, grouping of the hygiene products 10 takes place during the transfer by a plurality of hygiene products 10 namely being pushed into a respective compartment 17 of the compressing apparatus 16 in order to form a group 20 of hygiene products 10.

Figure 2:
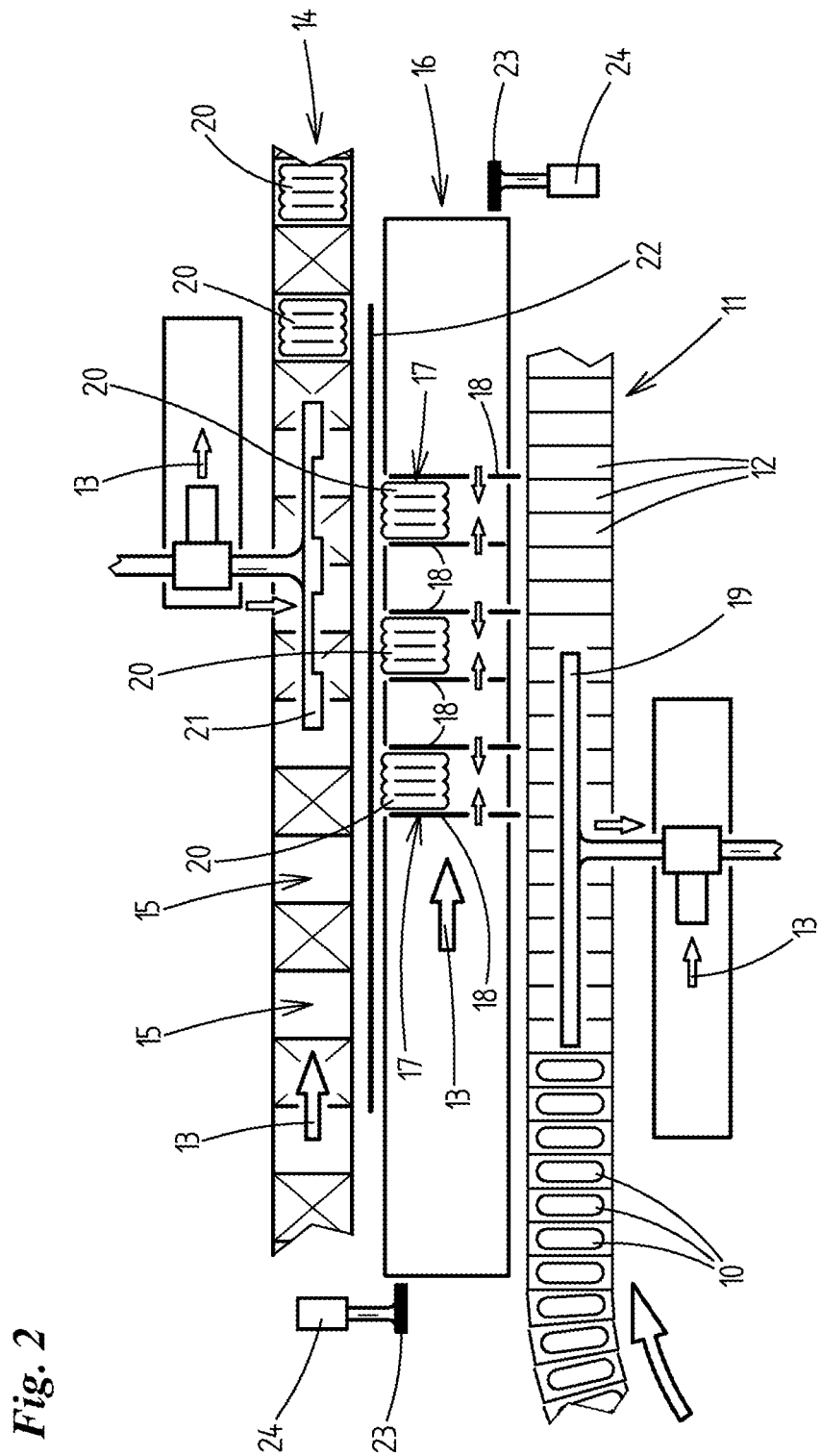
Figure 3:
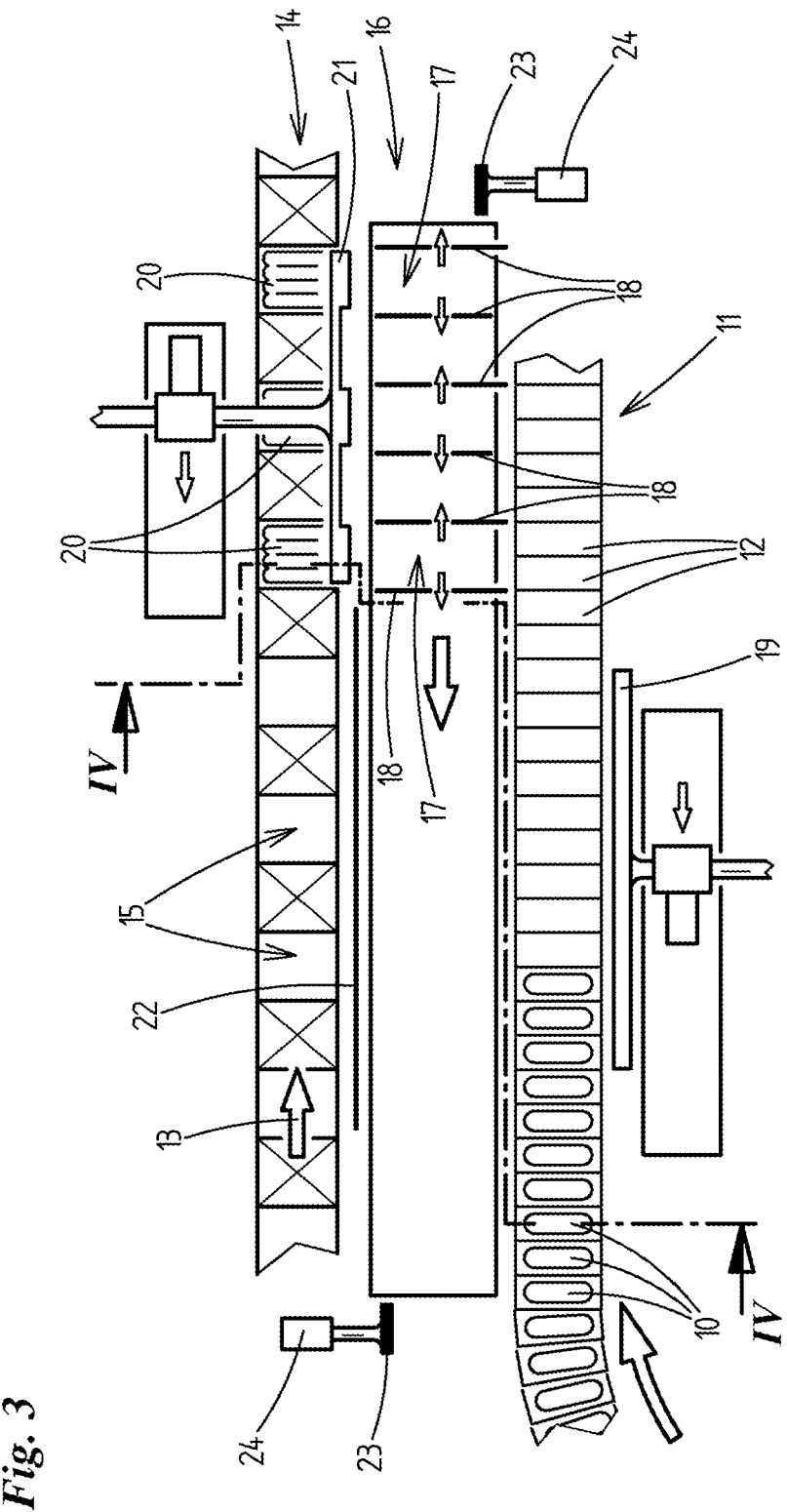

During the further transporting of the groups 20, the latter are compressed in the compressing apparatus 16. To do this, the walls 18, limiting the compartments 17 laterally, of each compartment 17 are moved toward each other in order to compress the groups 20. Because this takes place during the continuous movement of the compartments 17 in the transport direction 13, the corresponding movements of the walls 18 are superimposed with the movement of the compartment 17. In other words, the walls 18 and the compartment 17 are also moved toward each other during the movement in the transport direction (FIG. 2).

After the groups 20 have been compressed, the transfer to the compartments 15 of the second conveyor 14 takes place. An extraction member 21, which extracts a plurality of groups 20 of hygiene products 10 simultaneously into compartments 15 of the second conveyor, is used for this purpose. This also takes place during the continuous transporting. The compartments 17 and 15 are correspondingly moved together with the extraction member 21 in the transport direction 13 during the transfer.

The extraction member 21 here works in the manner of a scraper which draws the groups 20 from the compartments 17 and into the compartments 15, is then raised and moved back to the starting position in order to extract the next groups 20.

A further special feature consists in the compressing apparatus 16 being able to serve to equalize different speeds of the first conveyor 11 and the second conveyor 14.

It is, for example, conceivable that the compartments 12 of the first conveyor 11 and the compartments 17 of the compressing apparatus 16 are first moved synchronously with one another such that the hygiene products 10 can be transferred and that the compartments 17 of the compressing apparatus 16 are then moved synchronously with the compartments 15 of the second conveyor 14 in order to transfer the groups 20. This then entails both matching the speeds and also aligning the compartments 12, 15, and 17 relative to one another.

Alternatively, the compressing apparatus 16 and the first conveyor 11 and the second conveyor 14 can also be operated at the same speed and with compartments 12, 15, and 17 aligned relative to one another.

The implementation of the superimposed movements of the compressing apparatus 16 is effected by means of belts which are driven by servomotors. It should be understood that means other than belts or servomotors can be used within the scope of the invention such that reference can also be made below to a transmission means 23 (for example, a belt) which couples the drive 24 (for example, a servomotor) to the walls 18 of the compressing apparatus 16. For this purpose, the walls 18 can be fastened to the belts which are each displaced by a separate drive 24 (see FIG. 4). Guide rails 25 which are used for the guided movement of the respective walls 18 are also illustrated in FIG. 4. This guidance can, however, also be implemented by other structural solutions.

In particular the following variants are conceivable with regard to the driving of the walls 18:

In one variant 1 which falls under the above description, two separate belts are employed, each with an independent drive 24. In each case two groups of walls 18 are fastened to the belts. Driving via the two servomotors enables, on the one hand, the spacing between the individual walls 18 (compression spacing) to be changed and, on the other hand, all the walls 18 to be moved in a directed fashion for the purpose of synchronous operation with the first conveyor 11 and the second conveyor 14.

The number of the fastened walls 18 can vary and depends on the number of groups 20 to be compressed. A disadvantage of this variant can, however, be that the mutual spacing between the walls 18 for the second conveyor 14 (spacing of the compartments 15 from one another in the second conveyor 14) is fixed. This means that for a different mutual spacing on the second conveyor 14, the mutual spacing between the walls 18 would also have to be adapted in terms of format on the belts.

A variant 2 not illustrated in the drawings relates to an exemplary embodiment of a mechanical coupling of the walls 18. Only the two outer walls 18 are here driven via belts and the other walls are mechanically connected. In this variant, the mutual spacing of the compartments 17 is variable but this depends on the compression spacing. This means that when the compression spacing changes (for example, because of a different number of hygiene products 10 between the walls 18), the mutual spacing on the second conveyor 14 also has to be adapted.

Figure 6:
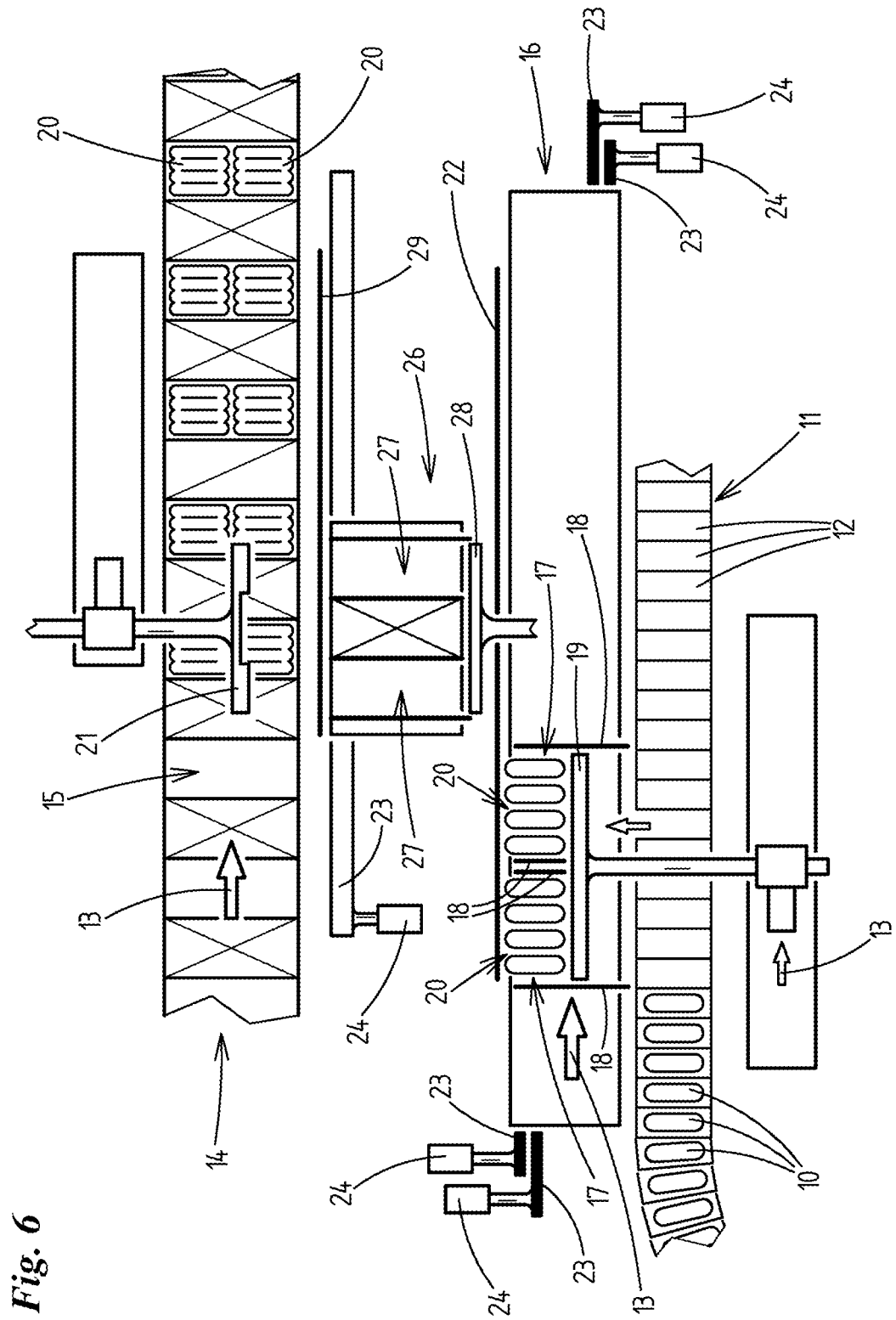
FIGS. 6 to 9 show an alternative device for forming compressed groups of hygiene products in a plan view during successive phases of the movement sequence.
Figure 7:
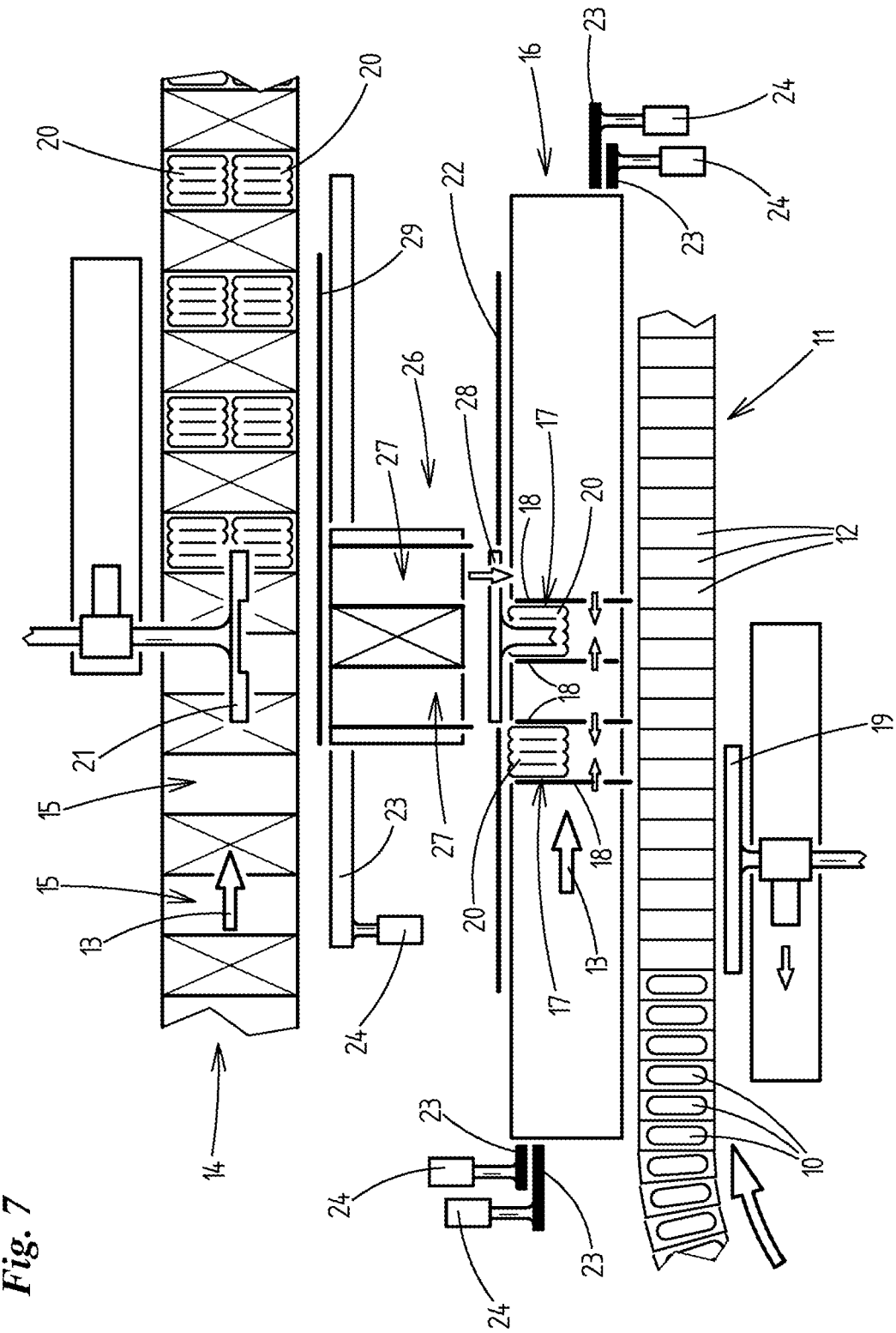
Figure 8:
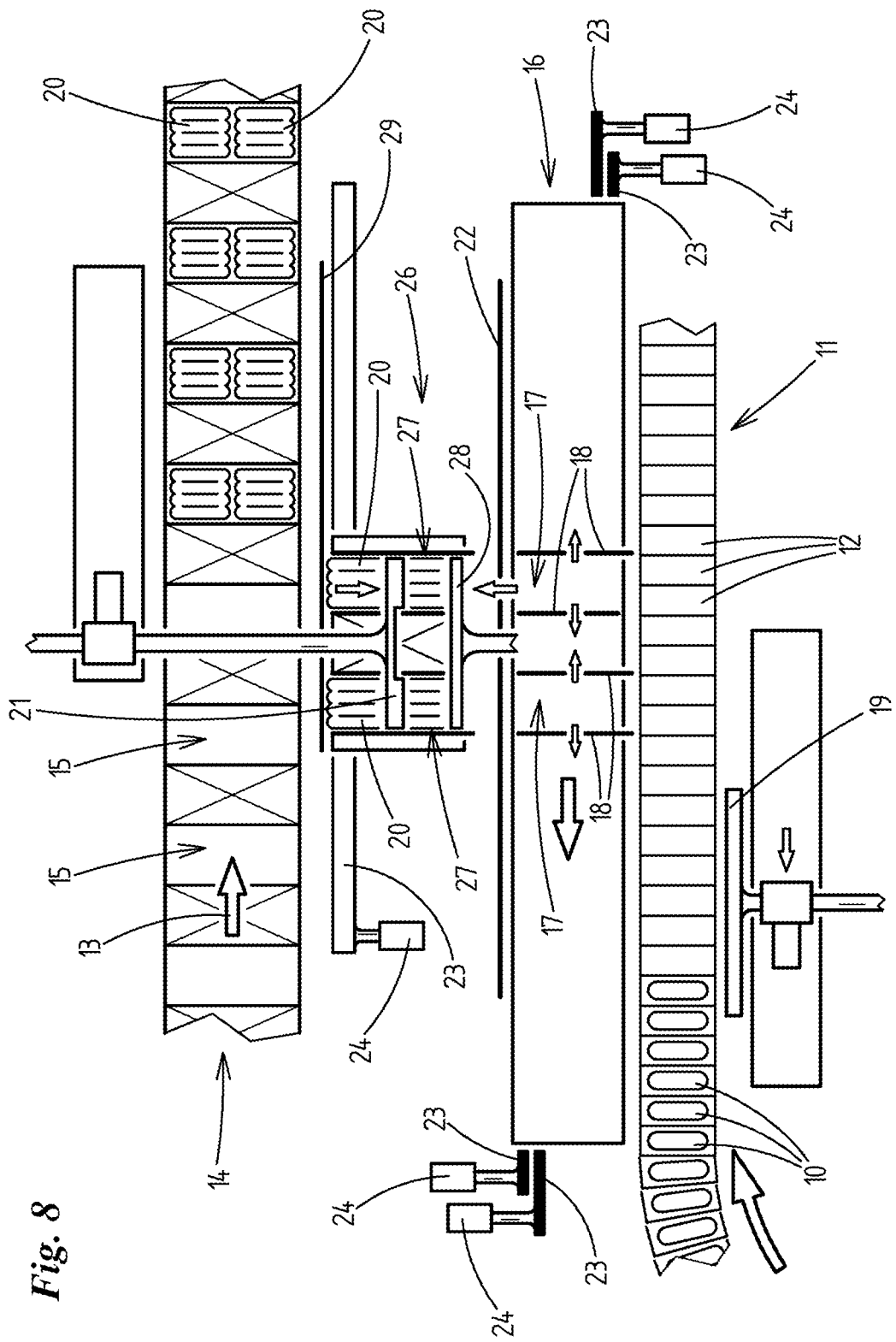
Figure 9:
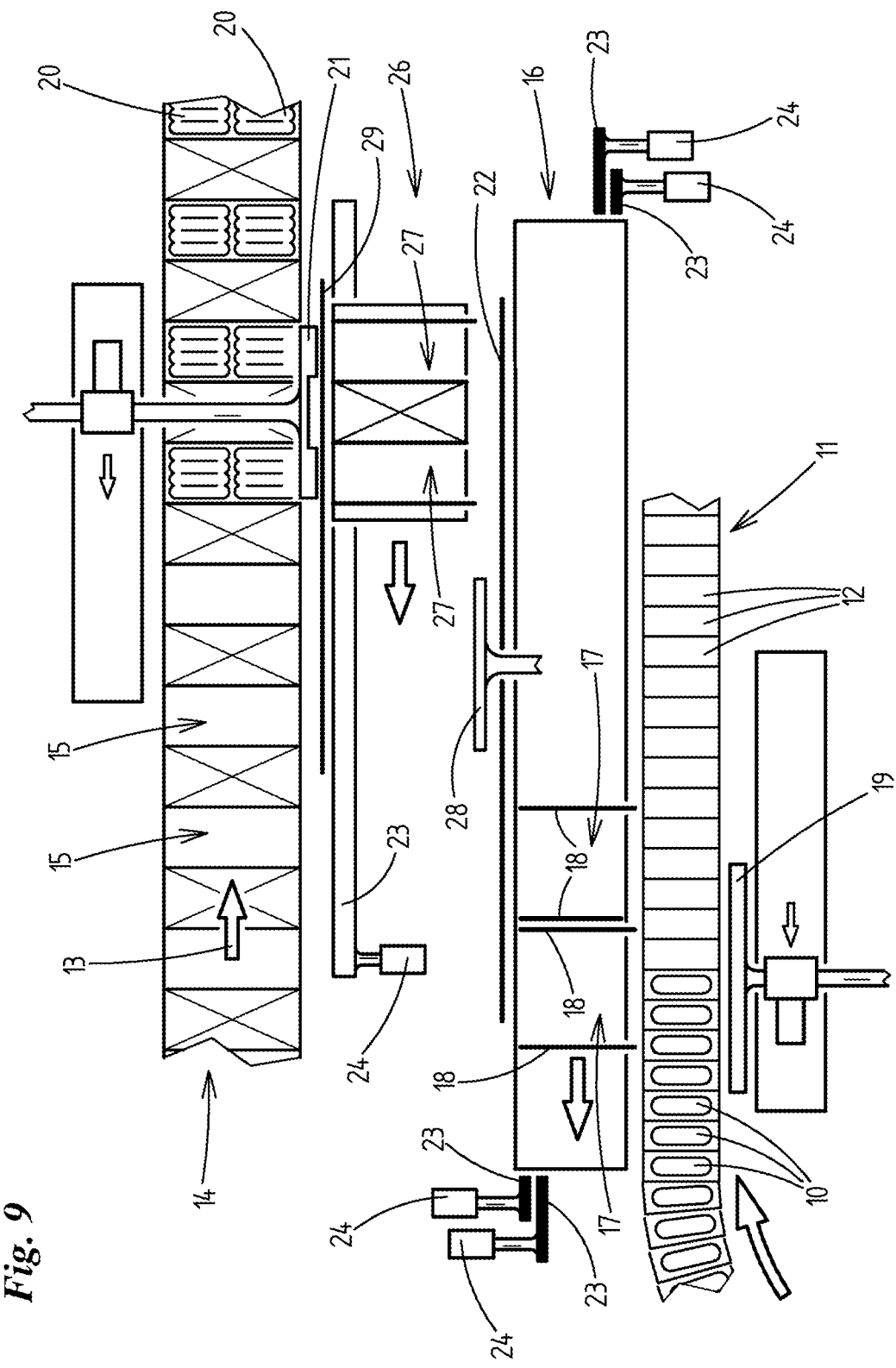

A variant 3 which is shown in FIG. 6 can be employed to increase the flexibility with respect to the compression spacing and mutual spacing. Here each wall 18 is fastened on an independent belt which is driven separately by a drive 24. As a result, all the spacings can be set in a fully flexible manner. This means that all the compression spacings of the walls 18 relative to one another can be regulated and also the spacings between the compartments 17 can be adapted completely to the mutual spacing on the second conveyor 14.

A further advantage of this variant 3 consists in the fact that more walls 18 can be present in the compressing apparatus 16 from the outset than is currently required. Thus, for example, eight walls 18 (required for compressing four groups 20) can be installed in advance. Only two of these walls 18 are not driven ("taken out of operation") when only three groups 20 of hygiene products 10 are to be compressed as a required format.

It is true for all variants that the components can be adapted to the different numbers of groups by rapid format changeovers.

The detail shown in FIG. 1 (illustrated enlarged in FIG. 5) shows the special structural feature that the walls 18 engage inside one another when they form the compartments 17 for receiving the uncompressed groups 20. This has the advantage that the walls 18 are arranged in a space-saving fashion and can form a compartment 18 which is as large as possible.

It was described above that the device is configured to move in each case a plurality of hygiene products 10 or groups 20 simultaneously between the first conveyor 11 or the compressing apparatus 16 and the second conveyor 14. It should be understood, however, that within the scope of the invention this can also be omitted such that just one product 10 or one group 20 is always moved at the same time. It is moreover conceivable that a plurality of hygiene products 10 but just a single group 20 is or are transferred, and vice versa.

An alternative device for forming compressed groups of hygiene products is shown in FIGS. 6 to 9.

A difference from the first exemplary embodiment according to FIGS. 1 to 5 that needs to be mentioned is that a grouping apparatus 26 is arranged between the compressing apparatus 16 and the second conveyor 14.

The grouping apparatus 26 can also be moved parallel to the compressing apparatus 16 and the second conveyor 14 in the transport direction 13. To do this, a drive 24 and a transmission means 23 are in turn provided. The grouping apparatus 26 moreover also has a plurality of compartments 27 which serve to receive groups 20 of compressed hygiene products 10.

The pushing of the individual hygiene products 10 from the first conveyor 11 is effected as described above and is illustrated in FIG. 6. The compressing of the groups 20 of hygiene products in the compressing apparatus 16 is likewise identical to the above method (see FIG. 7).

The transfer of first groups 20 to the grouping apparatus 26 takes place following the compressing step. For this purpose, the compartments 17 of the compressing apparatus 16 are aligned with the compartments 27 of the grouping apparatus 26. A second pusher 28 pushes in each case a first group 20 from the compartments 17 of the compressing apparatus 16 into the compartments 27 of the grouping apparatus until they come to bear against a second stop 29. To do this, the first stop 22 of the compressing apparatus 16 is lowered in order to free up the transfer path. The same procedure is followed for the transfer of second groups 20 of compressed hygiene products 10 (see FIG. 8) which then come to rest in the compartments 27 of the grouping apparatus 26 together with the first groups 20.

The grouping apparatus 26 is then synchronized with the second conveyor 14. This means that the grouping apparatus 26 is accelerated to the speed of the second conveyor 14 and the compartments 27 are aligned with the compartments 15 of the second conveyor 14.

The extraction member 21 which is here likewise employed to transfer the groups 20 is moved at the speed of the second conveyor 14. This means that the grouping apparatus 26, the extraction member 21, and the second conveyor 14 run (at the same speed) in a synchronized fashion in the transport direction 13.

The extraction member 21 then (during the continuous uniform movement of the elements) draws the groups 20 into a compartment 15 of the second conveyor 14 by means of which they can then be conveyed onward to the packaging process.

As soon as the transfer of the two layers of the compressed sanitary towels has been effected, the grouping apparatus 26 and the extraction member 21 return to their starting position. The compressing apparatus 16 can already have moved on its travel to the starting position previously (after the transfer of the last group 20 to the grouping apparatus 26). At the same time, the walls 18 here move apart from one another again and thus form the compartments 17 for renewed transfer of the uncompressed hygiene products 10 by the first pusher 19 (see FIG. 9).

Each wall 18 can preferably also be separately fastened here to an individual belt and each of these belts can be driven independently via a servomotor. In addition to controlling the movements, the format of the desired delivery/compression size can be adapted by the independent actuation of the belts (and the corresponding walls 18) which is thus possible (change in the number of products in the individual groups, compression ratio/spacing). Adaptation to the mutual spacing of the compartments 15 of the second conveyor 14 can thus also be performed.

This adaptation can be necessary when the compartments 17 of the compressing apparatus have a different mutual spacing than the compartments 15 of the second conveyor 14. The walls can moreover also be guided by guide rails 25 (or other structural solutions). The number of walls 18 (and hence of the compartments formed) is also variable here.

A further advantage of the grouping apparatus 26 is that it is ensured that the compartments 15 of the second conveyor 14 are always completely filled (and hence also that the cardboard boxes are always completely filled). It may happen that a compartment 12 of the first conveyor 11 is empty (for example, because a faulty hygiene product 10 has been rejected upstream). The first pusher 19 transfers the individual hygiene products 10 into the compressing apparatus 16 only when the groups 20 can be fully formed. If the groups 20 are already fully/completely present in the grouping apparatus 26, the grouping apparatus 26 waits until a second full number of groups 20 has been delivered from the compressing apparatus 16 and pushed into the grouping apparatus 26. Only then does the transfer to the second conveyor 14 take place. Thus, although there can be empty compartments 15 of the second conveyor 14 (and accordingly also later empty cardboard boxes) because the second conveyor 14 is moved continuously during the waiting period, there is no risk of final incomplete packages (only partially filled cardboard boxes) being produced.

LIST OF REFERENCE NUMERALS

10 (hygiene) product
11 first conveyor
12 compartment (first conveyor)
13 transport direction
14 second conveyor
15 compartment (second conveyor)
16 compressing apparatus
17 compartment (compressing apparatus)
18 wall (compartment of compressing apparatus)
19 (first) pusher
20 group (of products)
21 extraction member
22 stop
23 transmission means
24 drive
25 guide rail
26 grouping apparatus
27 compartment (grouping apparatus)
28 (second) pusher
29 stop

The invention claimed is:

1. A method for forming groups (20) of compressed hygiene products (10), wherein uncompressed hygiene products (10) are supplied by a continuously driven first conveyor (11) and are transferred from the first conveyor (11) to a compressing apparatus (16) during the continuous transporting, wherein the compressing apparatus (16) has at least one compartment (17) for a group (20) of uncompressed hygiene products (10), and wherein in each case a plurality of uncompressed hygiene products (10) are transferred from the first conveyor (11) into the at least one compartment (17) of the compressing apparatus (16) whilst the at least one compartment (17) is moved continuously, together with the first conveyor (11), in a transport direction (13) of the first conveyor (11), wherein the group (20) of uncompressed hygiene products (10) is compressed in the at least one compartment (17) during the continuous transporting in the transport direction (13) such that, after compression, a group (20) of compressed hygiene products (10) is situated in the at least one compartment (17) of the compressing apparatus (16), and wherein the group (20) of compressed hygiene products (10) is discharged to at least one compartment (15) of a second conveyor (14) during the further continuous transporting of the at least one compartment (17) of the compressing apparatus (16) in the transport direction (13), wherein the at least one compartment (17) of the compressing apparatus (16) is moved continuously in the transport direction (13) with the at least one compartment (15) of the second conveyor (14), wherein, when the compressed hygiene products (10) are discharged from the compressing apparatus (16), in each case a plurality of groups (20) of compressed hygiene products (10) are transferred simultaneously to a plurality of adjacent compartments (15) of the second conveyor (14) whilst the at least one compartment (17) of the compressing apparatus (16), together with the compartments (15) of the second conveyor (14), are moved continuously in the transport direction (13).

2. The method as claimed in claim 1, wherein the at least one compartment (17) of the compressing apparatus (16) is limited laterally by opposite walls (18) of the compressing apparatus (16) which are moved toward each other in order to compress the group (20) of uncompressed hygiene products (10) whilst the compartment (17) is moved continuously in the transport direction (13).

3. The method as claimed in claim 1, wherein the at least one compartment (17) of the compressing apparatus (16) is moved respectively synchronously with the first conveyor (11) or the second conveyor (14) continuously in the transport direction (13) in order to receive the uncompressed hygiene products (10) and/or discharge the compressed hygiene products (10).

4. The method as claimed in claim 1, wherein, during the transfer of the uncompressed hygiene products (10) to the compressing apparatus (16), in each case a plurality of adjacent compartments (17) of the compressing apparatus (16) are filled simultaneously with a plurality of hygiene products (10) whilst the compartments (17) are moved continuously, together with the compartments (12) of the first conveyor (11), in the transport direction (13), and in that the hygiene products (10) situated in the adjacent compartments (17) are then compressed simultaneously.

5. The method as claimed in claim 1, wherein the compressing apparatus (16) equalizes differences in speed between the first conveyor (11) and the second conveyor (14), wherein the difference in speed can also be equal to zero such that the first conveyor (11) and the second conveyor (14) are driven in the transport direction (13) at the same speed.

6. The method as claimed in claim 5, wherein the first conveyor (11) and the second conveyor (14) are driven in the transport direction (13) at a matching speed, and in that the compartments (17) of the compressing apparatus (16) are moved at the same speed in the transport direction (13) when receiving the uncompressed hygiene products (10) and when discharging the compressed hygiene products (10).

7. The method as claimed in claim 5, wherein the first conveyor (11) and the second conveyor (14) are driven in the transport direction (13) at different speeds, and in that the at least one compartment (17) of the compressing apparatus (16) is, when receiving the uncompressed hygiene products (10) and discharging the compressed hygiene products (10), moved in the transport direction (13) at a speed which corresponds respectively to the speed of the first conveyor (11) and of the second conveyor (14).

8. The method as claimed in claim 1, wherein the compressing of the hygiene products (10) takes place exclusively in the compressing unit (16), and in that there is no upstream or downstream pre-compressing or post-compressing.

9. The method as claimed in claim 2, wherein the movement of the walls (18) of the at least one compartment (17) of the compressing apparatus (16) is superimposed with the transporting of the at least one compartment (17) in the transport direction (13) during the compression of the group (20) of hygiene products in the at least one compartment (17).

10. The method as claimed in claim 1, wherein the uncompressed hygiene products (10) are transferred from the first conveyor (11) to the compressing apparatus (16) by means of a first pusher (19), wherein the uncompressed hygiene products (10) are pushed away, transversely to the transport direction (13) of the first conveyor (11) and of the compressing apparatus (16), by means of the first pusher (19).

11. The method as claimed in claim 1, wherein the at least one group (20) of compressed hygiene products (10) is pulled out from the compartments (17) of the compressing apparatus (16) and across onto the second conveyor (14) by means of an extraction member (21), wherein the group (20) of compressed hygiene products (10) is pulled across by means of the extraction member (21) transversely to the transport direction of the compressing apparatus (16) and of the second conveyor (14).

12. The method as claimed in claim 1, wherein the product flow on the first conveyor (11), in the compressing apparatus (16), and on the second conveyor (14) runs in mutually parallel paths at least in the respective transfer region of the uncompressed hygiene products (10) or the at least one group (20) of compressed hygiene products (10).

13. The method as claimed in claim 1, wherein a grouping apparatus (26), which continuously runs at least temporarily in the transport direction (13), is provided between the compressing apparatus (16) and the second conveyor (14), wherein the grouping apparatus (26) has at least one compartment (27) into which groups (20) of compressed hygiene products (10) coming from the compressing apparatus (16) are pushed, wherein the grouping apparatus (26) or the at least one compartment (27) thereof and the compressing apparatus (16) of the at least one compartment (17) thereof are stationary during the transfer.

14. The method as claimed in claim 13, wherein the plurality of groups (20) of compressed hygiene products (10) are transferred one after the other to the compartment (27) of the grouping apparatus (26) by a second pusher (28) in such a way that the groups (20) are arranged one behind the other in the pushing direction.

15. The method as claimed in claim 13, wherein the plurality of groups (20) of compressed hygiene products (10) are together pulled out from the compartment (27) of the grouping apparatus (26) and across onto the second conveyor (14) by the extraction member whilst the grouping apparatus (26) or the at least one compartment (27) thereof is moved continuously in the transport direction (13) together with the second conveyor (14) or the at least one compartment (15) thereof.

16. The method as claimed in claim 13, wherein in each case a plurality of groups (20) of compressed hygiene products (10) are transferred simultaneously from adjacent compartments (17) of the compressing apparatus (16) to the grouping apparatus (26) and/or from the grouping apparatus (26) to the second conveyor (14).

17. A device for forming groups (20) of compressed hygiene products (10), with a continuously driven first conveyor (11) for supplying uncompressed hygiene products (10), and with a compressing apparatus (16) for receiving the uncompressed hygiene products (10) from the first conveyor (11) during the continuous transporting, wherein the compressing apparatus (16) has at least one compartment (17) for a group (20) of uncompressed hygiene products (10), and wherein the device is configured to transfer in each case a plurality of uncompressed hygiene products (10) from the first conveyor (11) into the compartment (17) of the compressing apparatus (16) whilst the at least one compartment (17) is moved continuously, together with the first conveyor (11), in the transport direction (13) of the first conveyor (11), wherein the device is configured to compress the group (20) of uncompressed hygiene products (10) in the at least one compartment (17) of the compressing apparatus

(16) during the continuous transporting in the transport direction (13) such that, after compression, a group (20) of compressed hygiene products (10) is situated in the at least one compartment (17) of the compressing apparatus (16), and wherein the device is moreover configured to discharge and transfer simultaneously a plurality of groups (20) of compressed hygiene products (10) to a plurality of adjacent compartments (15) of a second conveyor (14) during the further continuous transporting of the at least one compartment (17) of the compressing apparatus (16) in the transport direction, wherein the at least one compartment (17) of the compressing apparatus (16) is moved continuously in the transport direction together with the plurality of adjacent (15) of the second conveyor (14).

18. The device as claimed in claim 17, wherein the at least one compartment (17) of the compressing apparatus (16) is limited laterally by opposite walls (18) of the compressing apparatus (16), and in that the walls (18) of the at least one compartment (17) can be moved toward each other by one or more drives (24) in order to compress the group of uncompressed hygiene products (10).

19. The device as claimed in claim 18, wherein the two opposite walls (18) of the at least one compartment (17) are each coupled to a transmission means (23), in particular a belt, which can be driven by in each case one independent drive (24) associated with the respective transmission means (23) in order to move the walls (18) of the at least one compartment (17).

20. The device as claimed in claim 19, wherein, in the case of a compressing apparatus (16) with a plurality of compartments (17), first walls (18) of each compartment (17) are coupled to a first transmission means (23) and second walls (18) of each compartment (17) are coupled to the second transmission means (23) such that two groups of walls (18) are formed which in each case can be moved together by drives (24) associated with the transmission means (23).

21. The device as claimed in claim 19, wherein, in the case of a compressing apparatus (16) with a plurality of compartments (17), each wall (18) of each of the compartments (17) is coupled to a separate independent transmission means (23) which can be driven by an independent drive (24) in order to individually move each wall (18) of all the compartments (17).

22. The device as claimed in claim 19, wherein adjacent walls (18) of adjacent compartments (17) of the compressing apparatus are formed so that they engage inside each other in a space-saving manner.

* * * * *